United States Patent [19]

Luckman

[11] Patent Number: 4,926,847
[45] Date of Patent: May 22, 1990

[54] SURGICAL CUTTING BLOCK

[75] Inventor: Thomas Luckman, Lakeville, Mass.

[73] Assignee: Johnson & Johnson Orthopaedics, Inc., New Brunswick, N.J.

[21] Appl. No.: 290,545

[22] Filed: Dec. 27, 1988

[51] Int. Cl.⁵ .............................................. A61F 5/04
[52] U.S. Cl. ....................................................... 606/88
[58] Field of Search ................... 128/303 R, 305, 317, 128/92 E, 92 V, 92 VV, 92 VY, 92 VW

[56] References Cited

U.S. PATENT DOCUMENTS

| | | | |
|---|---|---|---|
| 4,457,307 | 7/1984 | Stillwell | 128/92 VW |
| 4,467,801 | 8/1984 | Whiteside | 128/303 R |
| 4,474,177 | 10/1984 | Whiteside | 128/303 R |
| 4,487,203 | 12/1984 | Androphy | 128/303 R |
| 4,566,448 | 1/1986 | Rohr | 128/92 VW |
| 4,567,885 | 2/1986 | Androphy | 128/303 R |
| 4,567,886 | 2/1986 | Petersen | 128/92 VW |
| 4,703,751 | 11/1987 | Pohl | 128/303 R |
| 4,718,413 | 1/1988 | Johnson | 128/92 VW |
| 4,721,104 | 1/1988 | Kaufman et al. | 128/92 VW |
| 4,722,330 | 2/1988 | Russell et al. | 128/92 VW |
| 4,759,350 | 7/1988 | Dunn | 128/92 VW |
| 4,773,407 | 9/1988 | Peterson | 128/92 VW |

Primary Examiner—Robert A. Hafer
Assistant Examiner—Kerry Owens
Attorney, Agent, or Firm—Michael Q. Tatlow

[57] ABSTRACT

A cutting guide to position a bone cutting device is disclosed. The cutting guide has at least one fixed or stationary surface and a movable surface to create a slot or gap between the fixed surface and movable surface. The cutting device is positioned and held in the slot to make accurate bone cuts.

10 Claims, 4 Drawing Sheets

SURGICAL CUTTING BLOCK

FIELD OF THE INVENTION

The present invention relates to instruments that are used in surgical procedures to shape bone to accept implantable prothesis. Specifically, the present invention relates to cutting blocks used to shape bones or other hard tissue to receive components of a prosthesis and more specifically to a cutting block used to shape the distal femur to receive the components of a total knee prosthesis.

1. Background of the Invention

The implantation of an artifical joint prosthesis has become a widely used surgical procedure employed to correct problems caused by arthritis, trauma and general instability of various joints. In performing the surgical procedures used to implant such prostheses, it is necessary for the surgeon to remove bone to provide for the proper positioning and placement of the various components of such joint prostheses. Typical of such prostheses are implantable total knee prostheses. The total knee prosthesis consists of a femoral component which is fitted onto the distal end of the human femur, a tibial component and a patellar component. The tibial component is secured to the proximal end of the tibia and patellar component, which is a usually a plastic button which is inserted on the bone contact side of the patella, to prevent the patella from contacting the metal of the femoral and tibial component of the prosthesis. In placing the tibial component, the bone on the surface of the proximal tibial is removed to provide a generally uniform flat surface to receive the tibial component. In order to correctly place the femoral component, it is necessary to shape the distal end of the femur so that it very closely fits the femoral component of the total knee prosthesis. These are a number of different cutting steps at different angles which are necessary to shape the bone to correctly fit the prosthesis. In order to assist the surgeon in making these cuts, various bone cutting guides or blocks have been developed. These bone cutting guides or blocks are usually designed to cut the femur to accept a particular femoral component. Generally, the type of cuts that will be made are the same for all designs of femoral components of total knee prosthesis but the angles may differ for each particular prostheses. The first cut that is made is the cut of the distal femur. This first cut must be very accurate because the remaining cuts necessary to prepare the distal femur to receive the femoral component of the total knee prosthesis are based to some degree on the distal femur cut. The next cut that is made is on the anterior surface of the femur followed by a cut on the posterior surface of the femur. Generally, the next cuts are chamfer cuts which are at angles that will intersect the cut at the distal femur and the cuts on the anterior and posterior surface of the femur. In some cutting guide systems, a different guide is used for each of these cuts or sets of cuts. For example, a single guide may be used for the distal femur cut, another guide may be used for the anterior and posterior femoral cuts and a third guide might be used for the chamfer cuts. In some instances, the construction of the cutting guides are such that they can be used for either right of left knee surgery. In other instances, different cutting guides are used for the right knee and the left knee. Generally, the cutting guides provide a flat surface which can be used to guide the cutting instrument used by the surgeon in shaping the bone. the cutting instrument is either a hand-driven or power driven cutting device.

2. Prior Art

U.S. Pat. No. 4,474,177 to Whiteside discloses a series of cutting blocks used to cut the distal femur and which are aligned in a proper position by an intramedullary alignment guide.

U.S. Pat. No. 4,487,203 to Androphy discloses a triplanar knee resection guide which is used to cut the distal femoral condyles, the proximal tibia, and the distal femur.

U.S. Pat. No. 4,718,413 to Johnson discloses cutting guides that will engage both sides of a saw blade, that is, the saw blade will fit into a slot in the guide. There are a number of guides disclosed including a chamfer cutting guide and a distal femur cutting guide.

U.S. Pat. No. 4,721,104 to Kaufman et al. discloses a cutting guide which is used with a drill to make some of the the required cuts for the implantation of the femoral component of the total kneew prosthesis.

U.S. Pat. No. 4,722,330 to Russell et al. discloses a cutting guide which can be used in shaping the distal femur including the anterior and posterior cuts and the chamfer cut for the femoral component of a total knee prosthesis.

U.S. Pat. No. 4,759,350 to Dunn et al. discloses a cutting block or guide system which includes a guide block that can be used in cutting the anterior and posterior cuts and the chamfer cuts for a total knee prosthesis. The guide is fixed to the distal end of the femur after the distal femur cut has been made.

U.S. Pat. No. 4,773,407 to Peterson discloses a cutting guide system including a guide which has a slot through the guide to make the distal femur cut to prepare a bone to receive a femoral component of a total knee prosthesis.

SUMMARY OF THE INVENTION

One of the problems with the prior art cutting guides is that some of them furnish only a single guiding surface with which the surgeon could guide the cutting device use to cut the bone. If only a single cutting guide surface is used in the guide, the cutting device can easily move away from the guiding surface thereby losing the accuracy of the cut. Some of the cutting guides patents mentioned above disclose slots through which a cutting blade can be fit and if the blade is sized correctly for the slot, the slot would theoretically be capable of guiding both sides of the cutting blade. However, if a cutting blade of a different thickness is used, the blade would either be too large for the slot or too small for the slot and inaccurate cuts could result. Another problem with the prior art cutting guides was that when the guide is in the proper position, the guide will abstruct the surgeon's view of the bone to be cut. This is not desirable as the surgeon cannot visually determine the accuracy of the cut if his view of the bone is abstructed.

The cutting guide of the present invention is adjustable to accept cutting blades of various thickness and holds the blade tightly to make accurate cuts. The width of the slot in the guide can be adjusted after the cutting blade is in position to make accurate cuts. The guide is constructed so that the surgeon has an unobstructed view of the bone as it is cut. The preferred embodiment of the present invention specifically provides a cutting guide for making the distal femur, proximal tibia, anterior and posterior femur cuts and the anterior and posterior chamfers cuts in the distal femur. It will be clear to those skilled in the art that the present invention, as disclosed herein, can be modified to cut surfaces of other bones.

DETAILED DESCRIPTION OF THE INVENTION

Figure 1:
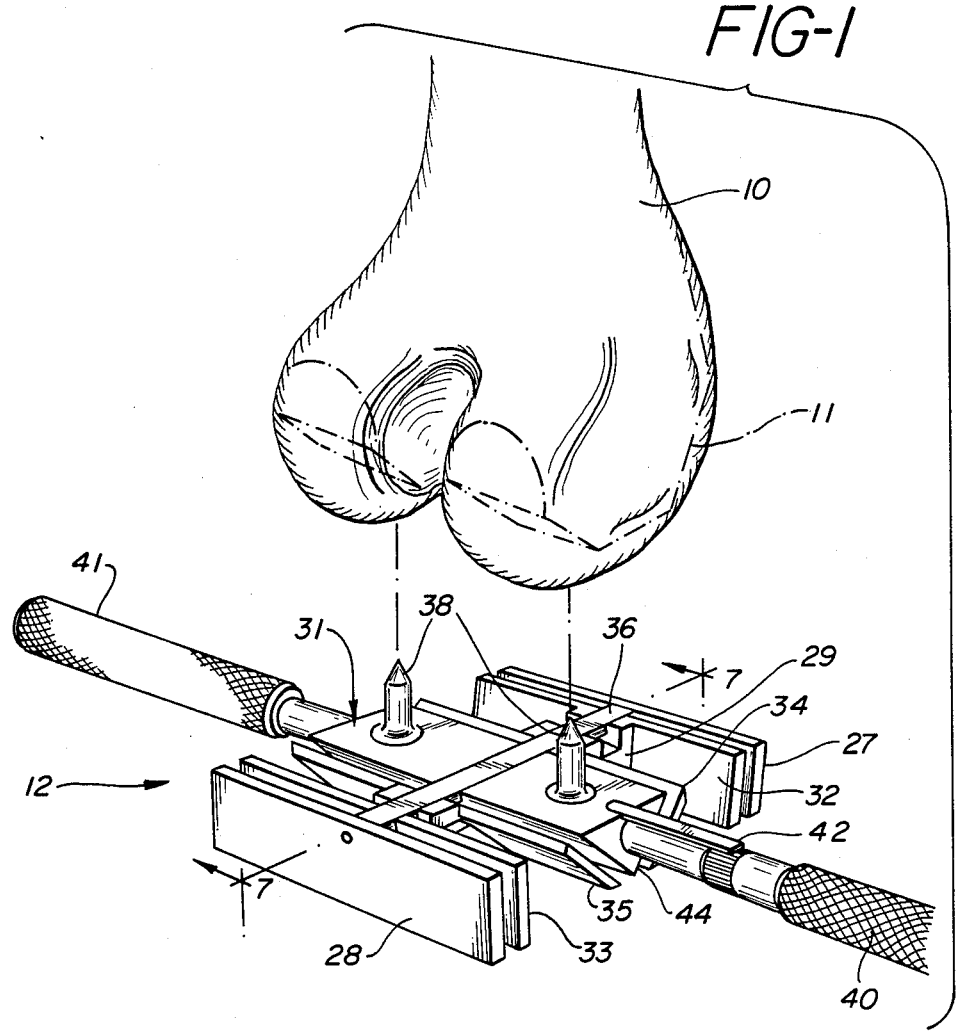
FIG. 1 is an perspective view showing the positioning of a cutting guide of the present invention used to cut the distal femur and the relationship of the cutting guide to the bone immediately before it is placed in contact with the bone.
Figure 2:
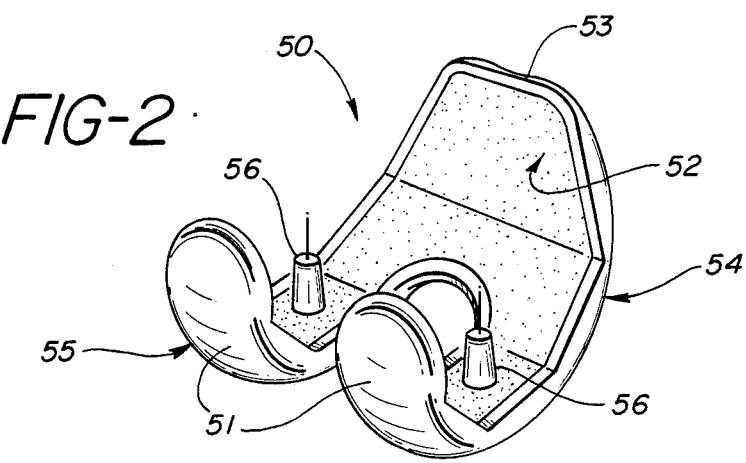
FIG. 2 is an perspective view of a typical femoral component of a total knee prosthesis.

Referring now to FIG. 1, there is shown the cutting guide of the present invention in a position in relationship to the distal femur 10 prior to the cutting of the bone. The dotted line 11 on the surface of the femur indicate the configuration of the femoral component of the knee prosthesis which would eventually be located in the dotted line position. A typical femoral component 50 is shown in FIG. 2. The femoral component comprises two condylar surfaces 51, the superior or outside portion 53 of which are curved to conform to curved surfaces on the tibial component (not shown) of the total knee prosthesis. The inferior surfaces 52 of the femoral component is fitted into the distal femur after the distal femur has been shaped to conform to the shape of the inferior surface. The anterior portion 54 of the femoral component is larger in size than the posterior portion 55 as the patella component will ride in a depression or groove on the anterior surface. The inferior surface 52 may be fitted with posts 56 which will be fitted into the femur to provide stability to the implanted prosthesis.

Figure 4B:
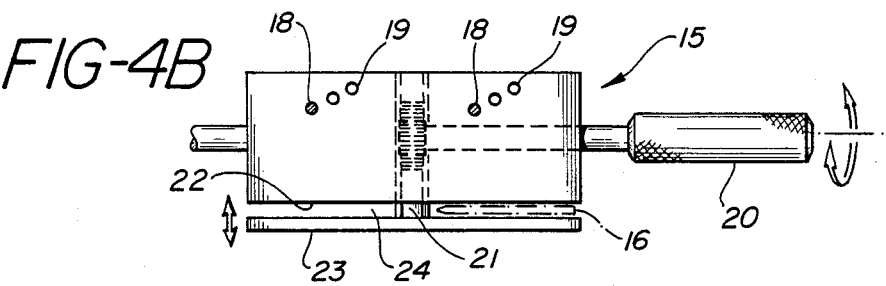
FIG. 4B is a front elevational view of the cutting block shown in FIG. 4A taken along line 4B—4B.
Figure 4A:
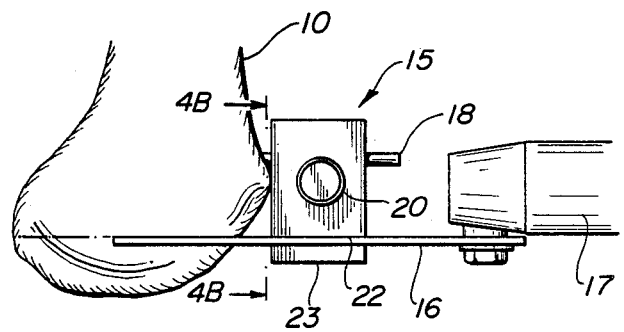
FIG. 4A is an side elevation of the position of a cutting guide for the first cut, the distal femur cut, in a femur to prepare the femur to receive the prosthesis.
Figure 5:
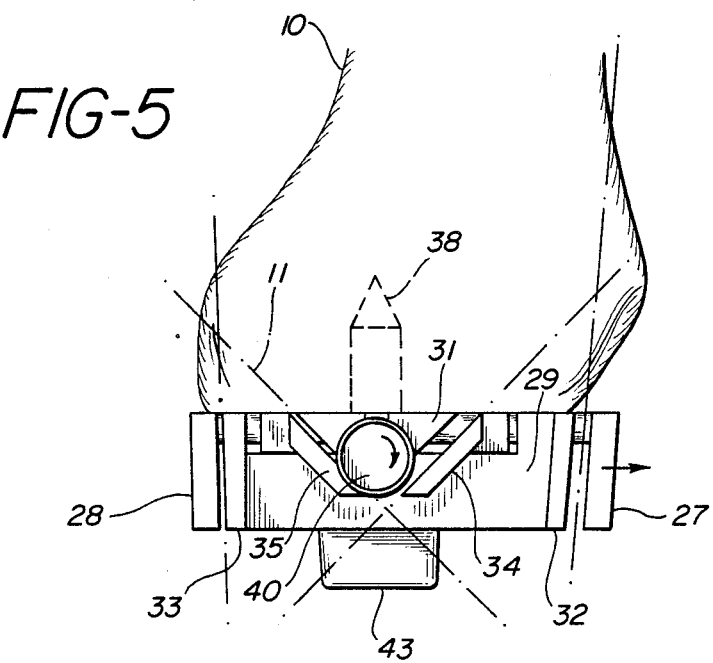
FIG. 5 shows the positioning of the cutting guide of the present invention on a femur and the direction of the cut lines which are made with the guide.

The cutting guides of the present invention comprise a stationary body portion and a movable portion. The space between the stationary body portion and movable portion can be adjusted to create a slot or gap into which a saw blade or other bone cutting device can be inserted. The movable portion can then be moved toward the stationary portion to narrow the slot or gap. The slot will be adjusted so the blade can readily reciprocate in the slot yet avoid excessive tipping of the blade. FIGS. 4A, and 4B show a cutting guide of the present invention of the type used in making the distal femur or proximal tibia cut. The guide 15 has a number of pins 18 which are used inserted through holes 19 in the guide to secure the guide in position on the bone. Usually two pins 18 are used and are placed in corresponding holes on each side of the guide. Multiple holes 19 are made in the block to adjust the cutting position of the guide. The guide has a stationary portion 22 and a movable plate 23. The movable portion is attached to the stationary portion 22 by a bar 21 by having a rack which meshes with a pinon on a handle 20. The rack and pinion are shown in dashed line in FIG. 4B. Rotation of the handle 20 will move the movable plate 23 toward or away from the stationary portion 22. These can be a second stationary handle, a portion 25 of which is shown, on the side of the guide opposite rotatable handle 20. A cutting blade 16, which is driven by a power source 17, is positioned in the gap 24 between the stationary 22 and movable 23 portions of the guide. The handle 20 is then turned to narrow the gap and secure the cutting blade in position. The position of the cutting blade in the gap 24 is shown in phantom in FIG. 4B.

The preferred embodiment of the cutting guide of the present invention, shown generally as 12 in FIG. 1 comprises a stationary body 31 having stationary inside plates 32 and 33 and a stationary central portion 44. There are movable angled plates 34 and 35, which are set at an angle which corresponds to the angled stationary portion 44 of the body 31 and movable outside plates 27 and 28. The plates 34 and 35 are capable of being moved toward and away from the stationary angled portion 44 of the body. The outside plates 27 and 28 are capable of being moved toward and away from the stationary plates 32 and 33. There is a dovetailed bar 36 to which the top and bottom outside plates 27 and 28 and the angled plates 34 and 35 are attached as will be further explained in detail. There are two spikes 38 secured to the central portion of the body. The spikes can be driven into the femur to position the cutting guide in the proper position. There is a pinion 39 which is fitted to the inner end of the handle 40 and is used to control the movement of the plates 34 an 35 and the plates 27 and 28. On the opposite end of the triangular portion of the body 44 there is another stationary handle 41 which is secured to the angular portion 44 of the body 31. There is a spring 42 which is affixed into the central portion of the body 44 and which maintains pressure on the movable handle 40 to maintain the handle in position. The stationary portion of the body 31 comprises the central angled portion 44, the stationary plates 32 and 33 and the stude 38 and handles 40 and 41 and a connector bar 29 to which the stationary components are joined. The movable plates 27, 28, 34 and 35 of the cutting guide are all connected by a dovetail bar 36 which can move in notches 37 cut in the stationary portion of the guide.

Figure 3:
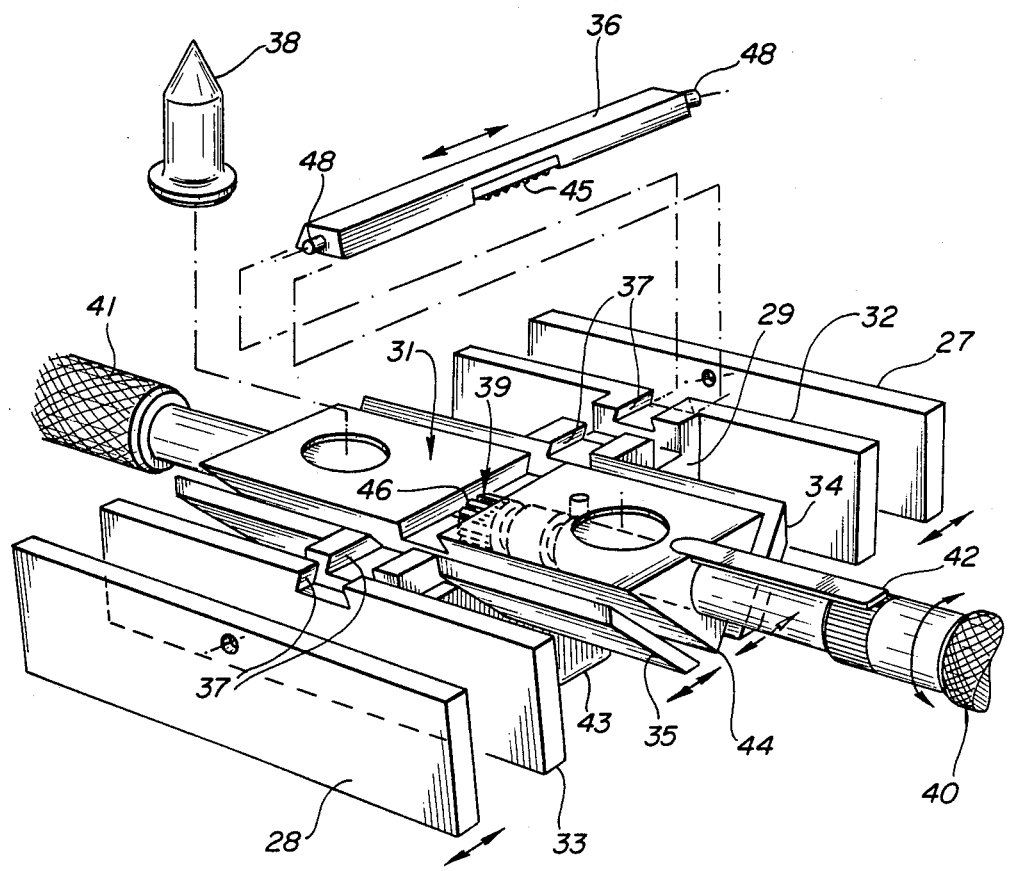
FIG. 3 is an exploded perspective view of the cutting guide of the present invention.

As shown in FIG. 3, the central portion of the dovetail bar 36 has teeth 45 cut into the bar, which teeth will mesh with teeth 46 cut in the end of the pinion 39. the dovetail bar has protrusions 48 at each end 48 which are fitted into the outside plates 27 and 28 to secure the plates to the dovetail bar.

There is an impact plate 43 affixed to the body of the guide opposite the spikes to allow the guide to be struck with a impact device to drive the spikes into the bone for the proper positioning of the guide on the femur.

Figure 7:
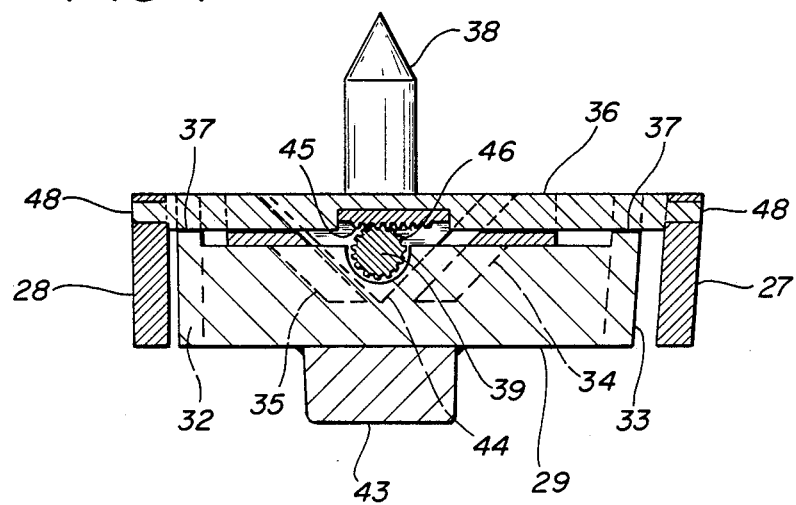
FIG. 7 is a cross-sectional view along the lines 7—7 of FIG. 1 showing the adjusting mechanism of the cutting guide of the present invention.

The turning of the handle 40 turns the pinion 39 which is attached to the handle. The teeth on the end of the pinion, best shown in FIG. 7, will turn the dovetail bar in the dovetail notch 37 which is cut into the body. This will move the outside movable plates 27 and 28 and the movable angled plates 34 and 35 and change the space between the plates and the stationary portions of the body. This space or slot can be adjusted to secure a cutting blade between the plates and the body. The slot formed by the plates and the body can then be adjusted to accept cutting blades or cutting devices of difference thicknesses. The stationary portions of the body are constructed to fix the angles at which the bone should be cut. It should also be noted that the cutting guide is relatively open so that the surgeon can see the position of the cutting blade in relation to the bone when the cut is made.

Figure 6:
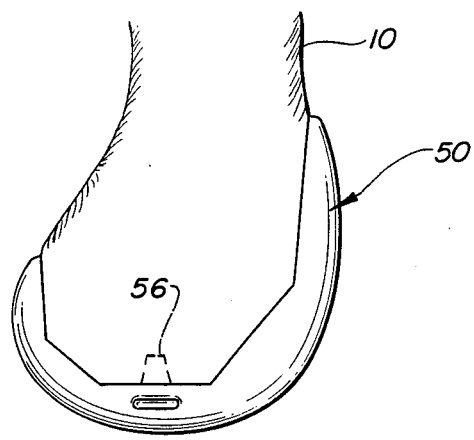
FIG. 6 shows the positioning of a prosthesis on the cut surface of the femur.

FIG. 6 shows the prosthesis of FIG. 2 in its position on the distal end of the femur after all of the cuts have been made.

The sequence of the cutting of the femur is shown in FIGS. 4A, 4B, 5 and 6. The first cut that is made in the femur is to cut the distal end of the femur to provide a flat surface on the distal end of the femur. A distal femoral cutting block 15 is positioned on the anerior surface of the femur and fixed to the femur with pins 18. The cutting blade 16 is placed against the stationary portion 24 of the cutting guide 22. The handle 20 is rotated, which moves the plate 23 toward the stationary portion 24 of the guide 22 creating a space 24 which allows the blade 16 to reciprocate but keeps the blade in position against the stationary portion 24 of the guide. A saw blade 16 driven by a power source 17 is guided by the cutting block 15 to make the required cut. When the cut is completed, the guide is removed from the bone by removing the pins.

The cutting guide 12 is then affixed in its proper position on the femur by impacting the impact plate to drive the spikes into holes previously drilled into the femur. The spikes in the cutting block are spaced to correspond to the posts 56 in the femoral component 50. The anterior and posterior cuts are then made. The cutting blade is positioned against the stationary plates and the slot wide adjusted by turning the handle 40. The cutting blade will fit into the slot formed by the space between the top plate and the body and the handle can be turned so the blade is properly positioned in the slot and the anterior cut is made. After the anterior cut is made, the handle can be turned to open the slot and the cutting blade removed. The handle will then be turned in the opposite direction to open the space between the bottom plate 33 and the body and the cutting blade would be inserted in the posterior slot, and the handle turned to bring the plates adjacent the cutting blade to make the posterior cut. After the posterior cut was made the chamfer cuts would be made following the same sequence, securing the cutting blade between the fixed angle portion 44 of the body 31 and the clamps 324 and 35. It should be noted that the anterior and posterior cuts are not necessarily made at an angle of 90° to the surface of distal femur cut. In the cutting guide shown in FIG. 5, the angle of the anterior cut is about 95° and the angle of the posterior cut is about 91° or 5° and 1° respectfully to an imaginary vertical line passing through the knee with the body in a standing position.

After all of the cuts are made the cutting guide can be removed and the femoral component can be fitted in place as shown in FIG. 6.

The use of the cutting guide in the present invention provides a simpler system of making accurate cuts to receive the femoral component of total knee prosthesis.

I claim:

1. A cutting guide to guide a cutting blade for cutting bone to receive a component of a prosthesis comprising a body having at least one stationary, relatively flat guiding surface, a movable plate having a relatively flat surface which is substantially parallel to said stationary guiding surface, means to move the movable plate towards and away from the stationary surface to create a space between the stationary guiding surface and the surface of the movable plate to receive a cutting blade and to maintain the cutting blade against the stationary surface.

2. The cutting guide of claim 1 further comprising means to maintain the guide in a fixed position on the bone structure to be cut.

3. The cutting guide of claim 1 further comprising a handle affixed to that part of the guide which contains the stationary guiding surface.

4. The cutting guide of claim 1 further comprising at least two stationary guiding surfaces and at least two movable plates to provide two different spaces to receive a cutting blade.

5. The cutting guide of claim 1 in which the movable plates are secured to a bar, said bar having teeth along a portion of its length, a pinion in contact with the teeth on said bar so that the rotation of the pinion will move the bar and the plates attached to the bar.

6. The cutting guide of claim 5 in which the pinion is at the end of a handle secured to the stationary portion of the guide.

7. The cutting guide of claim 1 further comprising pins to affix the cutting guide to the bone to be cut.

8. The cutting guide of claim 4 in which the stationary guiding surfaces are at different angles with respect to the bone to be cut.

9. The cutting guide of claim 4 which comprises at least four stationary guiding surfaces.

10. A cutting guide to guide a cutting device to make cuts in a distal femur to prepare the distal femur to receive the femoral component of a total knee prosthesis comprising:
a body having as two first fixed guiding surfaces which are set at angels to the bone to be cut of from 0° to 10°, two first movable surfaces movable attached to the body which are capable of being moved toward or away from the two first fixed surfaces to create slots to receive and position a cutting device with respect to the bone to be cut; two second fixed guiding surfaces which are set at an angle of 40° to 50° to the bone to be cut, two second movable surfaces attached to the body which are capable of being moved toward or away from the two second fixed surfaces to create slots to receive and position a cutting device with respect to the bone to be cut.

* * * * *